United States Patent [19]

Otterness

[11] Patent Number: 4,861,794
[45] Date of Patent: Aug. 29, 1989

[54] 3-SUBSTITUTED-2-OXINDOLE-1-CARBOXAMIDES AS INHIBITORS OF INTERLEUKIN-1 BIOSYNTHESIS

[75] Inventor: Ivan G. Otterness, Ledyard, Conn.

[73] Assignee: Pfizer Inc., New York, N.Y.

[21] Appl. No.: 181,131

[22] Filed: Apr. 13, 1988

[51] Int. Cl.$^4$ .............................................. A61K 31/40
[52] U.S. Cl. .................................... 514/414; 514/418
[58] Field of Search ................................ 514/414, 418

[56] References Cited

U.S. PATENT DOCUMENTS

| | | | |
|---|---|---|---|
| 4,556,672 | 12/1985 | Kadin | 514/418 |
| 4,569,942 | 2/1986 | Kadin | 514/418 |
| 4,677,132 | 6/1987 | Hayward | 514/411 |
| 4,678,802 | 7/1987 | Kadin | 514/418 |
| 4,725,616 | 2/1988 | Kadin | 514/414 |

FOREIGN PATENT DOCUMENTS

87/04618  8/1987  PCT Int'l Appl. .

OTHER PUBLICATIONS

Hayward, M., et al., "Mechanisms of Bone Loss: Rheumatoid Arthritis, Periodontal Disease and Osteoporosis", Agents and Actions, 22, 251–254 (1987).
Hayward, M., et al., Annual Reports in Medicinal Chemistry, 22, Sect. IV, Chapter 17, pp. 172–177 (1987).
Dinarello, C. A., "An Update on Human Interleukin-1: From Molecular Biology to Clinical Relevance", J. Clin. Immunol., 5, 285–297 (1985).
Camp, R.D. et al., "Psoriatic Skin Lesions Contain Biologically Active Amounts of an Interleukin 1-Like Compound", J. Immunol., 137, 3469–3474 (1986).
Dinarello, C. A., "Biology of Interleukin 1", FASEB J., 2, 108–115 (1988).
Dinarello, C. A., et al., "The Influence of Lipoxygenase Inhibitors on the In Vitro Production of Human Leukocytic Pyrogen and Lymphocyte Activating Factor (Interleukin-1)", Int. J. Immunopharmac., 6, 43–50 (1984).
Dinarello, C. A. et al., "Role of Arachidonate Metabolism in the Immunoregulatory Function of Human Leukocytic Pyrogen/Lymphocyte-Activating Factor/Interleukin 1", Immunol., 130, 890–895 (1983).
Pages 6–8 of the Presentation by Barry M. Bloom to Analysts of First Boston, New York City, New York on Sep. 10, 1987.
F–D–C Reports, Sep. 28, 1987, p. 11.
"Three Pfizer Drugs Promising; FDA Okay to be Sought in '89", Chemical Marketing Reporter, Sep. 14, 1987, p. 7.
F–D–C Reports, Sep. 14, 1987, p. 2.
Kunkel, S. L. et al., "Arachidontic Acid Metabolites Regulate Interleukin-1 Production," Biochemical and Biophysical Res. Copmm., 128:892–897 (1985).
Smith, R. J. et al., "Human Neutrophil Activation with Interleukin-1," Biochemical Pharmacology, 36:3851–3858 (1987).

Primary Examiner—Douglas W. Robinson
Assistant Examiner—Roger Gobrogge
Attorney, Agent, or Firm—Peter C. Richardson; J. Trevor Lumb; Gregg C. Benson

[57] ABSTRACT

This invention relates to the use of certain 3-substituted-2-oxindole-1-carboxamides of the formula

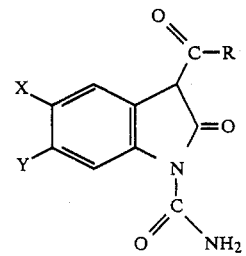

and the pharmaceutically-acceptable base salts thereof wherein X is H, Cl or F; Y is H or Cl; and R is benzyl or thienyl to inhibit interleukin-1 biosynthesis in a mammal. This invention also relates to the use of such compounds for treating interleukin-1 mediated disorders and dysfunctions such as bone and connective tissue metabolism disorders and immune dysfunction in a mammal. The methods of this invention comprise administering an interleukin-1 biosynthesis inhibiting amount of the compounds and salts of this invention to such a mammal.

45 Claims, No Drawings

3-SUBSTITUTED-2-OXINDOLE-1-CARBOXA-MIDES AS INHIBITORS OF INTERLEUKIN-1 BIOSYNTHESIS

BACKGROUND OF THE INVENTION

1. Field of the Invention

This invention relates to the use of certain 3-substituted-2-oxindole-1-carboxamides and the pharmaceutically-acceptable base salts thereof to inhibit interleukin-1 biosynthesis in a mammal. This invention also relates to the use of such compounds for treating interleukin-1 mediated disorders and dysfunctions such as bone and connective tissue metabolism disorders and immune dysfunction in a mammal. The methods of this invention comprise administering an effective amount of the compounds and salts of this invention to such a mammal.

2. General Background

Certain 3-substituted-2-oxindole-1-carboxamides of the formula

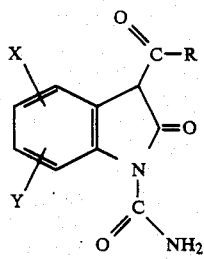

and the pharmaceutically-acceptable base salts thereof wherein, inter alia, X is H, Cl or F; Y is H or Cl; and R is benzyl or thienyl are disclosed and claimed in U.S. Pat. No. 4,556,672 which is assigned to the assignee hereof. That patent discloses that those compounds, in addition to being useful as antiinflammatory and analgesic agents, are inhibitors of both the cyclooxygenase (CO) and lipoxygenase (LO) enzymes. The teachings thereof are incorporated herein by reference.

Interleukin-1 (IL-1) has been reported to stimulate bone resorption both in vitro and in vivo. Hayward, M. and Fiedler-Nagy, Ch., Agents and Actions, 22, 251–254 (1987). It is also reported therein that IL-1, inter alia, induces the production of prostaglandin $E_2$ ($PGE_2$). $PGE_2$ is a stimulator of bone resorption and has been implicated in bone loss. Hayward, M. A. and Caggiano, T. J., Annual Reports in Medicinal Chemistry, 22, Sect. IV, Chapter 17, 172–177 (1987). Osteoporosis is defined as a debilitory loss of bone mineral which results in higher fracture rates. See Hayward, M. A. and Caggiano, T. J., supra, and references cited therein.

Interleukin-1 has been reported to be involved in the pathogenesis of many diseases. See Dinarello, C.A., J. Clin. Immunol., 5, 287–297 (1985), the teachings of which are incorporated herein by reference. Further still, elevated levels of IL-1 like material have been found to be associated with psoriasis. Camp, R.D., et al., J. Immunol., 137, 3469–3474 (1986).

The non-steroidal anti-inflammatory agent etodolac, 1,8-diethyl-1,3,4,9-tetrahydropyrano[3,4-b]-indole-1-acetic acid, has been disclosed in U.S. Pat. No. 4,677,132 to lower $PGE_2$ and reduce bone resorption. Etodolac has the formula

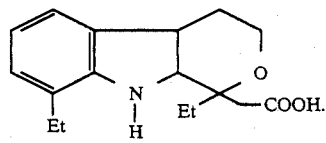

It has been reported that therapeutic levels of nonsteroidal antiinflammatory agents such as indomethacin and ibuprofen do not reduce IL-1 production. Similarly, cyclosporine A had no such effect. Corticosteroids, however, are effective in reducing IL-1 production. Dinarello, C.A., supra. Certain lipoxygenase inhibitors such as 5,8,11,14-eicosatetraynoic acid (ETYA) and 3-amino-1,3-trifluoromethylphenyl-2-pyrazoline (BW755C) have been reported to decrease in vitro production of leukocytic pyrogen (putative IL-1) from human monocytes. Dinarello, C.A., et al., Int. J. Immunopharmac., 6, 43–50 (1984).

However, until the invention herein, there was no report of use or intent to use the compounds or salts of this invention to inhibit IL-1 biosynthesis independent of lipoxygenase inhibition and to treat IL-1 mediated disorders and dysfunctions such as certain bone and connective tissue metabolism disorders and certain immune dysfunctions with such compounds nor any appreciation of their role in such treatments.

SUMMARY OF THE INVENTION

It has been found that certain 3-substituted-2-oxindole-1-carboxamides of the formula

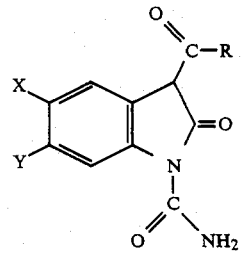

and the pharmaceutically-acceptable base salts thereof wherein X is H, Cl or F; Y is H or Cl; and R is benzyl or thienyl inhibit the biosynthesis of IL-1, independent of their lipoxygenase inhibiting activity, and thus are useful in treating IL-1 mediated disorders and dysfunctions such as certain disorders of bone and connective tissue metabolism and dysfunctions of the autoimmune system in mammals. Such bone metabolism disorders include, but are not limited to osteoporosis. By way of example and not of limitation, such connective tissue metabolism disorders include periodontal disease and tissue scarring. Further, examples of IL-1 mediated immune dysfunctions include, but are not limited to, allergy and psoriasis.

The methods of using the compounds and their pharmaceutically-acceptable base salts comprise administering to a mammal an effective amount of such compounds. Administration can comprise any known method for therapeutically providing a compound to a mammal such as by oral or parenteral administration as defined hereinbelow.

DETAILED DESCRIPTION OF THE INVENTION

The compounds of this invention which are of the formula

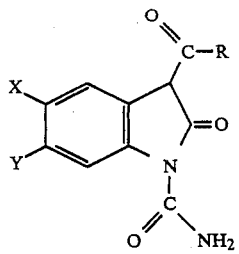

and the pharmaceutically-acceptable base salts thereof wherein X is H, Cl or F; Y is H or Cl; and R is benzyl or thienyl and the preparation thereof are disclosed in U.S. Pat. No. 4,556,672, the teachings of which are incorporated herein by reference. This invention concerns new uses for such compounds which comprise methods for inhibiting interleukin-1 (IL-1) biosynthesis in a mammal independent of inhibition of lipoxygenase. Also within the scope of this invention are methods of treating interleukin-1 mediated disorders and dysfunctions such as bone and connective tissue metabolism disorders and immune dysfunction.

Of the methods described above, preferred therein are those where the compound employed is of the formula above wherein X is Cl, Y is H and R is thienyl; those wherein in said compound X is F, Y is Cl and R is thienyl; those wherein in said compound X is F, Y is Cl and R is 2-thienyl; and those wherein in said compound X is H, Y is Cl and R is benzyl. Particularly preferred are methods wherein in said compound X is Cl, Z0 Y is H and R is 2-thienyl.

As disclosed in U.S. Pat. No. 4,556,672, the compounds of this invention hereinabove described are acidic and form base salts. All such base salts are within the scope of this invention and can be formed as taught by that patent. Such suitable salts, within the scope of this invention, include both the organic and inorganic types and include, but are not limited to, the salts formed with ammonia, organic amines, alkali metal hydroxides, alkali metal carbonates, alkali metal bicarbonates, alkali metal hydrides, alkali metal alkoxides, alkaline earth metal hydroxides, alkaline earth metal carbonates, alkaline earth metal hydrides and alkaline earth metal alkoxides. Representative examples of bases which form such base salts include ammonia, primary amines, such as n-propylamine, n-butylamine, aniline, cyclohexylamine, benzylamine, p-toluidine, ethanolamine and glucamine; secondary amines, such as diethylamine, diethanolamine, N-methylglucamine, N-methylaniline, morpholine, pyrrolidine and piperidine; tertiary amines, such as triethylamine, triethanolamine, N,N-dimethylaniline, N-ethylpiperidine and N-methylmorpholine; hydroxides, such as sodium hydroxide; alkoxides such as sodium ethoxide and potassium methoxide; hydrides such as calcium hydride and sodium hydride; and carbonates such as potassium carbonate and sodium carbonate. Preferred salts are those of sodium, potassium, ammonium, ethanolamine, diethanolamine and triethanolamine. Particularly preferred are the sodium salts.

Also within the scope of this invention are the solvates such as the hemihydrates and monohydrates of the compounds hereinabove described.

Interleukin-1 is known by those skilled in the art to exist in at least two forms which are referred to as the $\alpha$ and $\beta$ forms. Dinarello, C.A., FASEB J., 2, 108–115 (1988). As used throughout this specification and the appendant claims, the term interleukin-1 (IL-1) refers to all such forms of IL-1 including IL-1$\alpha$, IL-1$\beta$ and IL-1$\alpha$ and IL-1$\beta$ collectively.

The methods of this invention comprise administering the invention compounds and the pharmaceutically-acceptable base salts thereof to a mammal. Such compounds and their salts can be administered to said mammal either alone or, preferably, in combination with pharmaceutically-acceptable carriers or diluents in a pharmaceutical composition, according to standard pharmaceutical practice. Such administration can be oral or parenteral. Parenteral administration as used herein includes, but is not limited to, intravenous, intramuscular, intraperitoneal, subcutaneous, transdermal and topical including, but not limited to oral lavage, administration. However, it is generally preferred to administer such compounds and their salts orally.

In general, these compounds and their salts are most desirably administered in doses ranging from about 40 mg up to about 200 mg per day for oral administration and from about 1 mg up to about 200 mg per day for parenteral administration, although variations will still necessarily occur depending upon the weight of the subject being treated. The appropriate dose for inhibiting IL-1 biosynthesis in a mammal and for treatment of IL-1 mediated bone metabolism disorder, IL-1 mediated connective tissue metabolism disorder or IL-1 mediated immune dysfunction with the compounds and their salts of this invention will be readily determined by those skilled in the art of prescribing and/or administering such compounds. Nevertheless, it is still to be appreciated that other variations may also occur in this respect, depending upon the species of mammal being treated and its individual response to said medicament, as well as on the particular type of pharmaceutical formulation chosen and the time period and interval at which such administration is carried out. In some instances, dosage levels below the lower limit of the aforesaid range may be more than adequate, while in other cases still larger doses may be employed without causing any harmful or deleterious side effects to occur, provided that such higher dose levels are first divided into several smaller doses that are to be administered throughout the day.

For purposes of oral administration, tablets containing excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as, but not limited to, magnesium stearate, sodium lauryl sulfate and talc are often very useful for tableting purposes. Solid compositions of a similar type may also be employed as fillers in soft elastic and hard-filled gelatin capsules; preferred materials in this connection also include, by way of example and not of limitation, lactose or milk sugar as well as high molecular weight polyethylene glycols. When aqueous suspensions and/or elixirs are desired for oral administration, the essential active ingredient may be combined with various sweetening or flavoring agents, coloring matter or dyes and, if so desired, emulsifying and/or suspending agents, together with diluents such as water, ethanol, propylene glycol, glycerin and various like combinations thereof.

Although the preferred mode of administration of the compounds of this invention or their pharmaceutically-acceptable base salts is oral, they may be administered parenterally as well.

For purposes of parenteral administration, solutions of these particular compounds in sesame or peanut oil or in aqueous propylene glycol may be employed, as well as sterile aqueous solutions of the corresponding water soluble base salts previously enumerated. Such aqueous solutions should be suitably buffered if necessary, and the liquid diluent rendered isotonic with sufficient saline or glucose. These particular aqueous solutions are especially suitable for intravenous, intramuscular and subcutaneous injection purposes. In this connection, the sterile aqueous media employed are readily obtained by standard techniques well known to those skilled in the art. For instance, distilled water is ordinarily used as the liquid diluent and the final preparation is passed through a suitable bacterial filter such as a sintered glass filter or a diatomaceous-earth or unglazed porcelain filter. Preferred filters of this type include the Berkefeld, the Chamberland and the Asbestos Disk-Metal Seitz filter, wherein the fluid is sucked into a sterile container with the aid of a suction pump. Needless to say, the necessary steps should be taken throughout the preparation of these injectable solutions to insure that the final products are obtained in a sterile condition. For purposes of transdermal administration, the dosage form of the particular compound may include, by way of example, solutions, lotions, ointments, creams, gels, suppositories, rate-limiting sustained release formulations and devices therefor. Such dosage forms comprise the particular compound and may include ethanol, water, penetration enhancer and inert carriers such as gel-producing materials, mineral oil, emulsifying agents, benzyl alcohol and the like. Specific transdermal flux enhancing compositions are disclosed in pending U.S. patent application Ser. No. 925,641, filed Oct. 31, 1986, which is assigned to the assignee of this invention, the teachings of which are incorporated herein by reference. For purposes of topical administration, the dosage form of the particular compound may include, by way of example and not of limitation, solutions, lotions, ointments, creams and gels.

The ability of the compounds of this invention to inhibit interleukin-1 biosynthesis is demonstrated by the assay procedures described below.

C3H/HeN mice (Charles River, Wilmington, Mass.) are sacrificed by cervical dislocation and their abdomens sprayed with 70% ethanol to prevent bacterial contamination of the subsequent cellular preparation. Into the peritoneum of each mouse is injected 8 ml of RPMI[1] containing 5% FCS[2], penicillin-streptomycin (100 units/ml - 100 ug/ml) and glutamine (2mM). The peritoneum is kneaded to help free cells. Then, an incision through the skin of the abdomen is made to expose the underlying muscle layer. The peritoneal fluid is removed with a 20 gauge needle by inserting the needle, bevel down, through the exposed muscle layer just below the sternum. The peritoneal fluid from six mice is pooled in a plastic conical tube and microscopically examined for bacterial contamination. Uncontaminated fluid is centrifuged at about 600×g for six minutes and the supernatant decanted. The pelleted cells from five to six tubes are combined and resuspended in a total of 20 ml of RPMI-FCS[3]. The cell number is then ascertained using a hemacytometer and cell viability determined with Trypan Blue staining also using a hemacytometer. The cells are then diluted to $3 \times 10^6$ cells/ml using RPMI-FCS. To the wells of a 35 mm well plate is added 1 ml of the above cell suspension. The cells are incubated for 2 hours at 37° C. in a 5% $CO_2$ atmosphere to cause adherence of the macrophages to the walls of the wells. The supernatant is removed by swirling the wells vigorously and decanting. The adherent cells (i.e., macrophages) are washed twice with RPMI-SF[4]. To the wells containing adherent cells is added 1 ml of the compound under study at concentrations ranging from 0.1 to 100 ug/ml in RPMI-SF or 1 ml of RPMI-SF as a control. Then, 100 ml of LPS[5] in RPMI-SF (1 mg/5 ml) is added to each well. The plates are incubated at 37° C. in a 5% $CO_2$ atmosphere for 24 hours. The supernatants are removed and either assayed for IL-1 immediately or otherwise refrigerated or frozen for subsequent assay.

[1]RPMI-1640 medium (Hazelton Research Products, Inc., Lenexa, Kansas)
[2]Fetal calf serum which has been screened for good responsiveness to IL-1 in the thymocyte assay (Hyclone Laboratories, Logan, Utah) and for low spontaneous proliferation in the absence of IL-1.
[3]RPMI-1640 medium containing 5% fetal calf serum.
[4]RPMI containing penicillin-streptomycin (100 units/ml-100 ug/ml) and glutamine (2 mM).
[5]Refined purified lipopolysaccharide from *Salmonella minnesota* which has been checked to determine that the C3H/HeJ mouse is unresponsive thereto.

To assay for IL-1, 6-8 C3H/HeJ mice (Jackson Laboratories, Bar Harbor, Me.) are sacrificed by cervical dislocation and their thymuses removed asceptically. The thymuses are rinsed with four changes of media[6]. The thymuses are then teased apart to obtain a single cell suspension and the suspension filtered through 12 ply Johnson & Johnson sterile gauze (Johnson & Johnson Products, Inc., New Brunswick, N.J.). Following filtration, the cell suspension is centrifuged at 600×g for six minutes, the supernatant decanted and the cell pellet resuspended in 25 ml of media[6]. The cell density is determined using a hemacytometer and the cell viability determined using Trypan Blue staining followed by a cell count using a hemacytometer. The cells are then diluted to $2 \times 10^7$ cells/ml. Serial 2-fold dilutions of the LPS-stimulated supernatant obtained as described above are prepared in 96-well microtiter plates using media[6] as diluent (50 μl supernatant: 50 μl media per well). To each well is added 50 μl of $4 \times 10^{-5}$M 2-mercaptoethanol. Phytohemagglutinin P (Sigma Chemical, L-9132) (PHA) is added from a stock solution in media[6] such that 50 μl is added and the resulting concentration of PHA is 12 mg/ml. Then, 50 μl of the thymocyte suspension prepared as described above is added so that there is a final cell concentration of $5 \times 10^6$ cells/ml. The plates are incubated at 37° C. in a 5% $CO_2$ atmosphere for 54 hours. Then, tritiated thymidine (0.4 μCi in 10 μl media[6]) is added to each well and the plates incubated as described above for an additional 18 hours. Following the incubation, the cells are harvested on a cell harvester (Otto Hiller, Madison, Wis.) where the pellets are collected on strips of Whatman glass fiber filters (Whatman, Clifton, N.J.) and dried. The pellets are then counted using a beta scintillation counter in a toluene/omnifluor scintillation fluid. The amount of IL-1 present is proportional to the amount of tritiated thymidine in the pellets.

[6]Eagle's minimum essential medium with Earle's salts containing 6% fetal calf serum, 100 units/ml-100 ug/ml penicillin-streptomycin, 2mM glutamine, 0.1 mM nonessential amino acids (M.A. Bioproducts, Rockville, Md.) and 1 mM sodium pyruvate.

In addition to the foregoing thymocyte assay, the supernatants are assayed quantitatively for IL-1 according to the receptor binding assay described below. A standard curve is generated as follows. EL4-6.1 murine thymoma cells [10–15×10⁶ cells in 0.4 ml binding buffer (RPMI 1640, 5% FCS, 25 mM HEPES, 0.01% $NaN_3$, pH 7.3)] are added to varying amounts of unlabeled murine rIL-1α [recombinant IL-1α produced in *Escherichia coli* from the published sequence of amino acids 115–270 for IL-1α, Lomedico, P. M., et al., Nature, 312, 458–462 (1984)](40 pg to 40 ng in 0.5 ml buffer) and incubated for 1 hr at 4° C. with continuous shaking, after which 0.8 ng(0.1 ml) of human $^{125}$I-rIL-1β (New England Nuclear, Boston, Mass.) is added and shaking continued for an additional 3 hours. Samples are filtered with a Yeda apparatus (Linca Co., Tel-Aviv, Israel) through Whatman GF/C2.4 cm glass fiber filters (blocked with 0.5% powdered milk for 2 hrs at 37° C.) and washed once with 3 ml of ice-cold buffer. Filters are counted in a Searle gamma counter and non-specific binding is taken as the cpm bound in the presence of 200 ng unlabeled rIL-1α. A Hill calibration curve is constructed by plotting log (Y/100-Y) vs. log C where Y represents the percent of control $^{125}$I-rIL-1β binding and C is the concentration of unlabeled rIL-1α. A linear least-squares line is fitted through Y values between 20 to 80%. Then, to quantitate IL-1 levels in the supernatants obtained as described above, diluted supernatants replace rIL-1α in the above protocol and measured percent binding values are used to determine IL-1 concentrations from a standard Hill plot. Each dilution is assayed in duplicate and generally only dilutions with Y values between 20 to 80% are used to calculate average IL-1 levels.

Further, the adherent macrophages treated as described above are assayed for intracellular IL-1α according to Western blot analysis well known to those skilled in the art and as further described below. Adherent macrophages, treated as described above, are scraped from the wells of the well plate with a cell scraper. Cells from each treatment group are washed three times with phosphate buffered saline (PBS), then lysed with 0.5% NP-40 in phosphate buffer (50 mM KCl, 10 mM NaCl, 50 mM $KH_2PO_4$, 1.0 mM EDTA, pH 7.5) containing 10 mM di-isopropyl fluorophosphate (DFP) (Aldrich Chemical Co., Milwaukee, Wis.). Intact nuclei are pelleted and supernatants removed into clean microfuge tubes. Fifteen microliters (approximately 2×10⁵ cell equivalents) of each supernatant are dissolved in Laemmli sample buffer [Laemmli, U.K., Nature (Lond), 227, 680–685 (1970)] and applied to a 10–20% gradient polyacrylamide-SDS gel and electrophoresed at 35 mA constant current for 3–4 hours. Then, proteins are electroblotted from the gel to nitrocellulose (NC) paper (Micron Separations, Inc., Westboro, Mass.) by overnight transfer at 220 mA in 192 mM glycine, 25 mM Tris, 0.1% SDS, 25% methanol buffer. Replicate NC paper blots are overlayed with 1/250 dilutions of goat antiserum to murine rIL-1α and goat anti-murine rIL-1β [recombinant IL-1α(rIL-1α) produced in *Escherichia coli* from the published sequence of amino acids 115–270 for IL-1α, Lomedico, P. M., et al., Nature, 312, 458–462 (1984) and recombinant IL-1β(rIL-1β) produced in *E. coli* from the published sequence of amino acids 118–269 for IL-1β, Grey, P. W., et al., J. Immunol., 137, 3644–3648 (1986)]. After washing with 0.5% Tween 20 in PBS, the blots are probed with a 1/1000 dilution of horseradish peroxidase conjugated with swine antiserum to goat IgG (Boehringer Mannheim Biochemicals, Indianapolis, Ind.) and developed with the precipitating substrate 4-chloro-1-naphthol. An LKB laser densitometer (model 2220, LKB, Paramus, N. J.) is used to scan the lanes. Scanning data are quantified using LKB GelScan XL Evaluation software loaded into an AT&T PC 6300 computer.

When the macrophages described above were treated with the compound of this invention wherein X is Cl, Y is H and R is 2-thienyl in the presence of 3.3% fetal calf serum, the compound did not inhibit lipoxygenase as shown by the absence of inhibition of leukotriene ($LTC_4$) production as measured by radioimmunoassay with an $LTC_4[^3H]$RIA Kit (New England Nuqlear, Boston, Mass.) but did inhibit IL-1 production. The radioimmunoassay was performed in polypropylene tubes with all reagents diluted in 10 mM phosphate buffer, pH 7.4, containing 0.1% gelatin, 0.01 M EDTA, and 0.1% $NaN_3$. Fifty microliters each of supernatant, 4000 cpm tritiated tracer in assay buffer and dilute antisera were combined and incubated overnight at 4° C. Unbound radiolabeled tracer was removed by the addition of 250 μl of a suspension of 0.5% charcoal Norit A with 0.5% Dextran T-70. After centrifugation, 250 μl of supernatant were counted in 1.0 ml of Atomlight (New England Nuclear, Boston, Mass.) in 1.5 ml polypropylene microtubes with a Beckman LS-250 scintillation counter. The samples were quantitated by extrapolation from a log-logit standard curve (standards run in assay buffer).

What is claimed is:

1. A method of inhibiting interleukin-1 biosynthesis in a mammal which comprises administering to a mammal in need thereof an interleukin-1 biosynthesis inhibiting amount of a compound of the formula

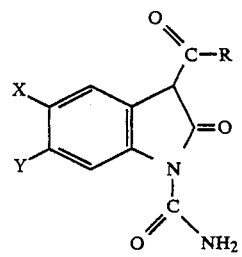

or a pharmaceutically-acceptable base salt thereof, wherein X is H, Cl or F; Y is H or Cl; and R is benzyl or thienyl.

2. The method according to claim 1 wherein X is Cl; Y is H; and R is thienyl.

3. The method according to claim 2 wherein R is 2-thienyl.

4. The method according to claim 3 wherein the pharmaceutically-acceptable base salt is sodium.

5. The method according to claim 1 wherein X is F; Y is Cl; and R is thienyl.

6. The method according to claim 5 wherein R is 2-thienyl.

7. The method according to claim 1 wherein X is H; Y is Cl; and R is benzyl.

8. The method according to claim 1 wherein the compound or a pharmaceutically-acceptable base salt thereof is administered orally.

9. The method according to claim 1 wherein the compound or a pharmaceutically-acceptable base salt thereof is administered parenterally.

10. A method of treating interleukin-1 mediated bone metabolism disorders in a mammal which comprises administering to said mammal an interleukin-1 mediated bone metabolism disorder treating amount of a compound of the formula

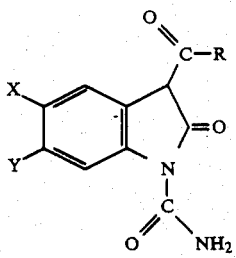

or a pharmaceutically-acceptable base salt thereof, wherein X is H, Cl or F; Y is H or Cl; and R is benzyl or thienyl.

11. The method according to claim 10 wherein X is Cl; Y is H; and R is thienyl.

12. The method according to claim 11 wherein R is 2-thienyl.

13. The method according to claim 12 wherein the pharmaceutically-acceptable base salt is sodium.

14. The method according to claim 10 wherein X is F; Y is Cl; and R is thienyl.

15. The method according to claim 14 wherein R is 2-thienyl.

16. The method according to claim 10 wherein X is H; Y is Cl and R is benzyl.

17. The method according to claim 10 wherein the compound or a pharmaceutically-acceptable base salt thereof is administered orally.

18. The method according to claim 10 wherein the compound or a pharmaceutically-acceptable base salt thereof is administered parenterally.

19. The method according to claim 10 wherein the bone metabolism disorder is osteoporosis.

20. The method according to claim 12 wherein the bone metabolism disorder is osteoporosis.

21. The method according to claim 13 wherein the bone metabolism disorder is osteoporosis.

22. A method of treating interleukin-1 mediated connective tissue metabolism disorders in a mammal which comprises administering to said mammal an interleukin-1 mediated connective tissue metabolism disorder treating amount of a compound of the formula

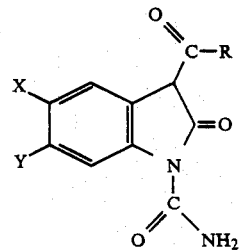

or a pharmaceutically-acceptable base salt thereof, wherein X is H, Cl or F; Y is H or Cl; and R is benzyl or thienyl.

23. The method according to claim 22 wherein X is Cl; Y is H; and R is thienyl.

24. The method according to claim 23 wherein R is 2-thienyl.

25. The method according to claim 24 wherein the pharmaceutically-acceptable base salt is sodium.

26. The method according to claim 22 wherein X is F; Y is Cl; and R is thienyl.

27. The method according to claim 26 wherein R is 2-thienyl.

28. The method according to claim 22 wherein X is H; Y is Cl; and R is benzyl.

29. The method according to claim 22 wherein the compound or a pharmaceutically-acceptable base salt thereof is administered orally.

30. The method according to claim 22 wherein the compound or a pharmaceutically-acceptable base salt thereof is administered parenterally.

31. The method according to claim 22 wherein the connective tissue metabolism disorder is periodontal disease or tissue scarring.

32. The method according to claim 24 wherein the connective tissue metabolism disorder is periodontal disease or tissue scarring.

33. The method according to claim 25 wherein the connective tissue metabolism disorder is periodontal disease or tissue scarring.

34. A method of treating interleukin-1 mediated immune dysfunction in a mammal which comprises administering to said mammal an interleukin-1 mediated immune dysfunction treating amount of a compound of the formula

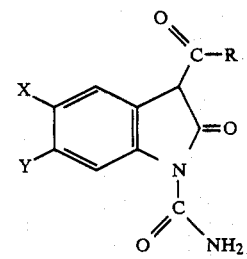

or a pharmaceutically-acceptable base salt thereof, wherein X is H, Cl or F; Y is H or Cl; and R is benzyl or thienyl.

35. The method according to claim 34 wherein X is Cl; Y is H; and R is thienyl.

36. The method according to claim 35 wherein R is 2-thienyl.

37. The method according to claim 36 wherein the pharmaceutically-acceptable base salt is sodium.

38. The method according to claim 34 wherein X is F; Y is Cl; and R is thienyl.

39. The method according to claim 38 wherein R is 2-thienyl.

40. The method according to claim 34 wherein X is H; Y is Cl; and R is benzyl.

41. The method according to claim 34 wherein the compound or a pharmaceutically-acceptable base salt thereof is administered orally.

42. The method according to claim 34 wherein the compound or a pharmaceutically-acceptable base salt thereof is administered parenterally.

43. The method according to claim 34 wherein the immune dysfunction is allergy or psoriasis.

44. The method according to claim 36 wherein the immune dysfunction is allergy or psoriasis.

45. The method according to claim 37 wherein the immune dysfunction is allergy or psoriasis.

* * * * *

UNITED STATES PATENT AND TRADEMARK OFFICE
CERTIFICATE OF CORRECTION

PATENT NO. : 4,861,794

DATED : August 29, 1989

INVENTOR(S) : Ivan G. Otterness

It is certified that error appears in the above-identified patent and that said Letters Patent is hereby corrected as shown below:

Column 3, line 38, delete "ZO" after"Cl,".

Signed and Sealed this

Seventeenth Day of July, 1990

*Attest:*

HARRY F. MANBECK, JR.

*Attesting Officer*  *Commissioner of Patents and Trademarks*